(12) United States Patent
Schwartz et al.

(10) Patent No.: US 12,226,326 B2
(45) Date of Patent: Feb. 18, 2025

(54) ABSORBABLE INTRAVASCULAR DEVICES THAT EXHIBIT THEIR GREATEST RADIAL STRENGTH AT THEIR NOMINAL DIAMETERS

(71) Applicant: EFEMORAL MEDICAL, INC., Los Altos, CA (US)

(72) Inventors: Lewis B. Schwartz, Lake Forest, IL (US); Ivan Tzvetanov, Mountain View, CA (US); Alex Etrada, Menlo Park, CA (US)

(73) Assignee: EFEMORAL MEDICAL, INC.

( * ) Notice: Subject to any disclaimer, the term of this patent is extended or adjusted under 35 U.S.C. 154(b) by 578 days.

(21) Appl. No.: 17/431,564

(22) PCT Filed: Feb. 21, 2020

(86) PCT No.: PCT/US2020/019132
§ 371 (c)(1),
(2) Date: Aug. 17, 2021

(87) PCT Pub. No.: WO2020/172480
PCT Pub. Date: Aug. 27, 2020

(65) Prior Publication Data
US 2022/0142799 A1 May 12, 2022

Related U.S. Application Data

(60) Provisional application No. 62/808,683, filed on Feb. 21, 2019.

(51) Int. Cl.
*A61F 2/915* (2013.01)
*A61F 2/90* (2013.01)
(Continued)

(52) U.S. Cl.
CPC ............... *A61F 2/915* (2013.01); *A61F 2/90* (2013.01); *A61F 2/958* (2013.01); *A61F 2/91* (2013.01);
(Continued)

(58) Field of Classification Search
CPC .... A61F 2/915; A61F 2/82; A61F 2/07; A61F 2/958; A61F 2210/0004; A61F 2/86;
(Continued)

(56) References Cited

U.S. PATENT DOCUMENTS

| 4,733,665 A | 3/1988 | Palmaz |
| 10,136,991 B2 | 11/2018 | Backus et al. |

(Continued)

FOREIGN PATENT DOCUMENTS

| JP | 2013505776 A | 2/2013 |
| JP | 2016535647 A | 11/2016 |
| WO | 2018067171 A1 | 4/2018 |

OTHER PUBLICATIONS

Extended European Search Report for application No. EP20760231.9 mailed on Oct. 14, 2022, 8 pages.

*Primary Examiner* — Suba Ganesan
(74) *Attorney, Agent, or Firm* — Convergence Intellectual Property Law P.C.; Jonathan Garfinkel

(57) ABSTRACT

Devices, systems, and methods are provided to maintain or enhance blood flow through the blood vessel. Balloon-expandable, bioresorbable, vascular stent elements configured to be implanted in the blood vessel are described herein. Stent elements comprise a closed cell pattern configured to provide their greatest radial strength at or near the diameters of their intended therapeutic use.

6 Claims, 12 Drawing Sheets

(51) Int. Cl.
*A61F 2/958* (2013.01)
*A61F 2/91* (2013.01)

(52) U.S. Cl.
CPC ............ *A61F 2210/0004* (2013.01); *A61F 2250/0039* (2013.01); *A61F 2250/0067* (2013.01)

(58) Field of Classification Search
CPC ...... A61F 2/90; A61F 2/91; A61F 2002/9155; A61F 9/90; A61F 2210/004
See application file for complete search history.

(56) References Cited

U.S. PATENT DOCUMENTS

| | | |
|---|---|---|
| 2002/0142119 A1 | 10/2002 | Seward et al. |
| 2006/0241739 A1 | 10/2006 | Besselink et al. |
| 2013/0317596 A1* | 11/2013 | Rapoza .................. A61L 31/06 623/1.16 |
| 2014/0364935 A1* | 12/2014 | Eli .......................... A61F 2/915 623/1.12 |
| 2015/0342764 A1* | 12/2015 | Ramzipoor ........... A61L 31/148 623/1.16 |
| 2017/0042672 A1 | 2/2017 | Backus et al. |
| 2017/0042706 A1 | 2/2017 | Denison et al. |

* cited by examiner

ABSORBABLE INTRAVASCULAR DEVICES THAT EXHIBIT THEIR GREATEST RADIAL STRENGTH AT THEIR NOMINAL DIAMETERS

CROSS REFERENCE TO RELATED APPLICATIONS

This application claims priority to U.S. provisional patent application No. 62/808,683 entitled ABSORBABLE INTRAVASCULAR DEVICES THAT EXHIBIT THEIR GREATEST RADIAL STRENGTH AT THEIR NOMINAL DIAMETERS filed on Feb. 21, 2019 and is incorporated herein by reference.

FIELD OF THE INVENTION

The present application pertains generally to the field of medical devices. More specifically, the present application pertains to the design and manufacture of intravascular stents intended to maintain patency (blood flow) of blood vessels (arteries and veins).

BACKGROUND

The pathological degeneration of arteries known as atherosclerosis is responsible for one-third of all human mortality. It represents a tremendous current and future human disease burden that will account for more than 23 million projected annual deaths by the year 2030. Atherosclerosis involving lower extremity arteries, known as peripheral arterial occlusive disease (PAOD) can be found in two-thirds of the population over 70 years old. Approximately 20% of patients present with symptoms, which, if left untreated, can lead to severe disability, limb loss and death. Furthermore, an estimated 11% of patients afflicted with PAOD primarily present with the most severe form of the disease: critical limb ischemia (CLI). CLI occurs when occlusive arterial plaques have become so numerous and extensive that the baseline perfusion of the extremity is inadequate to sustain its viability (gangrene). CLI carries an extremely poor prognosis; only about half of afflicted patients will be alive with viable limbs only six months after the diagnosis is made.

Traditional management of symptomatic PAOD consists of open surgical bypass of chronically diseased arterial segments. The results are often favorable; revascularization with autogenous vein confers ~70% primary graft patency and ~80% limb salvage at five years. However, while the durability of surgical bypass grafting has been thoroughly documented, so has its significant mortality and morbidity. Indeed, between 14 and 44% of surgical incisions made in territories of compromised vascular supply become infected, and up to 69% of patients treated with surgical revascularization sustain complications and/or require re-hospitalization during the first year.

With the primary goal of achieving effective mechanical revascularization with reduced procedural morbidity, percutaneous endovascular techniques including balloon angioplasty and stent implantation were popularized 1980s and established as a viable alternative treatment strategy in 2005. Unfortunately, their effectiveness has remained limited as up to 40% of conventional endovascular procedures will be complicated by arterial restenosis within the first year.

The mainstay of endovascular intervention for PAOD is percutaneous transluminal balloon angioplasty. Unfortunately, its salient effect on blood flow is only transient. Following dilatation, the inherent elasticity of the vessel causes it to recoil, returning it to its narrowed state and rendering the treatment ineffective. One often-cited analysis of contemporary clinical data suggests that one-year vessel patency following balloon angioplasty in long lesions is a dismal 28%.

In order to prevent recoil, provide more sustained radial dilatation and treat segmental arterial dissection secondary to angioplastic trauma, percutaneously deliverable metal scaffolds or "stents" were developed in the 1990s. The first stent type to be widely applied to the treatment of atherosclerotic plaques was a balloon-expandable stents (BES) designed as an open mesh tube comprised of stainless steel. When crimped onto an angioplasty balloon it could be advanced through the arterial tree coaxially and deployed directly within the plaque. Stent implantation created a larger and more durable flow channel as compared to balloon angioplasty alone. In the modern era, balloon-expandable stents are deployed in virtually every case of percutaneous coronary intervention (PCI) as well as many peripheral interventional procedures.

As the arterial lumen is always larger than the diameter of the crimped stent, the initial balloon and stent expansion occurs without contact to the arterial wall. When the expanding stent initially contacts the wall, the stretched artery begins to exert an opposing inward force on the expanding balloon and stent. Maximum inflation is generally maintained for 1-3 minutes in an attempt to relax the stretched artery. When the balloon is finally deflated and withdrawn, the tension generated within the expanded artery partially re-compresses the stent until an equilibrium is reached between the inwardly-directed arterial tension of the artery and the outward radial resistive force of the stent. The difference between the stent diameter at maximum balloon inflation and the stent diameter following balloon withdrawal is commonly referred to as the "stent recoil". BES are rigid and non-deformable medical devices; they are deployed by inflating their delivery balloon within the target lesion and embedding the rigid scaffold within the vessel wall. The final stent shape is casted by the deformation produced by the high-pressure balloon and held in place by the opposing collapsing force of the target artery. Its architecture is permanent; reimaging the device over time generally reveals no change in the diameter or shape that was achieved during the procedure.

Optimal metal stent design has been the subject of considerable research and debate. A generally accepted design property is that radial resistive force of a metal BES increases as the material quantity per unit area increases; i.e., the stent is stronger at smaller diameters. An example of this phenomenon is shown in FIG. 1. In this study, four commercially-available balloon-expandable coronary stents were expanded to their nominal diameters and placed in a circumferential radial force tester. The generated force was measured after compression of the stent with a 3.5 mm initial diameter at 0.1 mm/s until the diameter was reduced to 1.5 mm. The force was recorded and plotted on the ordinate using diameter as the abscissa. As seen in the FIG. 1, radial compression of the stent generates continually increasing force as the diameter decreases, the stent's geometry is compacted and the metal quantity per unit area increases. The forces generated at small diameters are clinically irrelevant, however, as the stent is deployed in the artery at or near its nominal diameter.

This same phenomenon has also been observed in bioresorbable stent design. Braided stents fabricated from monofilaments of poly(L-lactic acid) were inserted into a nonelastic, wrap-around collar. One end was fixed; the other was loaded with dead weights translating into a compressive radial pressure. The results are shown in FIG. 2. As expected, there was an approximate linear relationship between radial deformation and tension. The slope of the linear region was a function of both the initial stent diameter and the monofilament draw-ratio. The phenomenon that balloon-expandable stents are weakest at their diameter of intended use has been universally observed in the basic design of metal and resorbable stents.

Percutaneous balloon angioplasty and stent implantation is highly injurious to the arterial wall. These treatments are inherently mechanical in nature as the forces required to pry open arteries stiffened with firm plaque are considerable. Originally believed to impart a simple stretch force to the artery, more recent studies have demonstrated that these mechanical manipulations are most effective when creating traumatic cracks and fissures in the plaque, thus destroying the arterial architecture and rendering the vessel unable to recoil in the early post-procedure period. The result is a high degree of acute cellular and structural damage which, naturally, induces a physiologic local stress response.

Endovascular stent procedures fail because the pathological forces required to break the artery stimulate an intense proliferative response which, over time, creates new stenoses within the stent (in-stent restenosis or ISR). Also known as neointimal hyperplasia, the process of ISR is primarily mediated by vascular smooth muscle cells (SMCs), the principal cellular component of all blood vessels. SMCs are normally inert, with turnover of only about 0.1% cells/day. However, they become activated when perturbed by the process of percutaneous intervention. Activated SMCs chiefly originate from the media in areas of local trauma in the arterial wall, but also may be derived from circulating pluripotent progenitor cells that are attracted to sites of injury to differentiate into muscle-like progeny.

The initial stimulation and recruitment of SMCs from mechanical injury is further promulgated by growth factors and cytokines such as PDGF, FGF, EGF, and IGF-1 secreted by gathering and neighboring endothelial cells, platelets, and macrophages. This invokes a complex biochemical cascade within the SMC, eventually resulting in entry into the cell cycle and production of extracellular matrix. If enough cells are activated and divide, they build up an occlusive mass within the stent generating restenosis, thrombosis and, ultimately, therapeutic failure. Often likened to an aberrant healing response, the process is more analogous to the growth of a benign tumor within the stent. Restenosis, mediated by the pathological process of neointimal hyperplasia, complicates roughly 40% of all peripheral vascular interventions after one year, leading a consensus panel of cardiologists, vascular surgeons and interventional radiologists to suggest that the current state-of-the-art of superficial femoral artery (SFA) stenting results in only 62% patency after one year and that, for the SFA, there is no benefit over balloon angioplasty alone.

In addition to restenosis, other complications and limitations of contemporary metal stent technology are also occasionally observed. Stent fatigue and fracture has been reported to occur in virtually every treated vascular bed including the coronary, carotid, renal, iliac, femoropopliteal, infrapopliteal and venous systems. Pseudoaneurysm formation at the site of stent fracture has been reported, as has acute thrombosis and ischemia due to fracture and even frank rupture. Indwelling stents significantly complicate reintervention and can obscure interpretation of radiographic images, particularly computed tomograms. Finally, metallic stents are permanent and relatively rigid foreign bodies in the dynamic biological and hemodynamic environment of the peripheral vasculature; as such, they constitute a small but real threat throughout the lifetime of their host. Knowing their dangers, stent manufacturers make their balloon-expandable devices available only in limited lengths. Although atherosclerotic occlusions in peripheral arteries can be several hundred mm long, the longest available BES is only 60 mm. They are clearly inadequate for intervention in the leg where lesions >200 mm are routinely encountered.

Given the myriad shortcomings of currently available endovascular devices, "bioresorbable vascular scaffolds" (BVS) have emerged as a potential paradigm shift in percutaneous intervention. BVS offer the theoretical advantages of (1) effective scaffolding limiting post-dilation vessel recoil, (2) temporary implant attenuating chronic foreign body reaction and in-stent restenosis, (3) enhancing adaptive remodeling, (4) preserving vasoactive function and (5) facilitating intravascular imaging and surveillance.

Early versions of experimental bioresorbable scaffolds exhibited the "diameter-force relationship" that is typical of metal stents. FIG. 2 shows such a relationship for experimental absorbable stents fabricated by braiding monofilaments of PLLA into an open tubular structure using a Teflon core. As is typical of stents designed in this manner, their radial strength increased with reductions in diameter, similar to balloon-expandable metal stents.

Absorbable scaffolds may be actually better suited for the peripheral vasculature given its relatively high rate of interventional failure with conventional devices, its larger arterial diameters and longer lesions, its requirement for deformation with skeletal movement and its higher tolerance for thrombosis. Absorbable intravascular stents intended for implantation into the femoropopliteal can theoretically, (1) provide temporary scaffolding against arterial recoil, (2) obliterate endovascular injury-induced dissection, (3) prevent acute thrombosis, (4) smooth the flow channel to blunt cellular activation and interaction at the boundary wall, (5) extend patency beyond traditional balloon and/or metal stents and, (6) slowly dissolve allowing the vessel to more positively and naturally remodel.

Because the arterial diameter, length, pathology and motion differ markedly among human vasculatures, a device specifically designed for the periphery might be expected to perform better than devices designed for other anatomies.

Therefore, it would be advantageous to have a stent for use in vasculature that exhibits its greatest radial strength at its nominal diameter. At least some of these objectives will be met by the embodiments described below.

SUMMARY

The embodiments herein describe a device for placement within a blood vessel to maintain or enhance blood flow through the blood vessel. The device may comprise a balloon-expandable, bioresorbable, vascular stent element configured to be implanted in the blood vessel. The stent element may be formed from a bioresorbable polymer material. In an embodiment, the stent element is configured to have a compressed state with a first diameter while crimped on a delivery balloon and an expanded state with a second diameter greater than the first diameter after expansion and placement in the blood vessel. The stent elements comprise a closed cell pattern configured to provide a first radial resistive force in the compressed state and a second radial resistive force greater than the first radial resistive force in the expanded state. The closed cell pattern of the stent element is configured to provide a peak radial resistive force at a diameter substantially equal to the second diameter. In an embodiment the struts of the closed cell pattern are configured to have a substantially longitudinal alignment in the compressed state and a more circumferential alignment in the expanded state thereby providing greater radial resistive force in the expanded state than the compressed state.

In some embodiments, the stent may be formed from a material comprising poly(L-lactic acid) (PLLA), poly(D-lactic acid) (PDLA), poly(D,L-lactic acid) (PDLLA), semicrystalline polylactide, polyglycolic acid (PGA), poly (lactic-co-glycolic acid) (PLGA), poly(iodinated desamino tyrosyl-tyrosine ethyl ester) carbonate, polycaprolactone (PCL), salicylate based polymer, polydioxanone (PDS), poly(hydroxybutyrate), poly(hydroxybutyrate-co-valerate), polyorthoester, polyanhydride, poly(glycolic acid-co-trimethylene carbonate), poly(iodinated desaminotyrosyl-tyrosine ethyl ester) carbonate, polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, or combinations thereof.

In an embodiment, the stent comprises a therapeutic drug. The therapeutic drug may prevent or attenuate inflammation, cell dysfunction, cell activation, cell proliferation, neointimal formation, thickening, late atherosclerotic change or thrombosis.

In an embodiment, the radial rigidity of the stent is slowly attenuated as its structural polymer is unlinked and metabolized such that the stent slowly becomes more flexible causing adaptation and remodeling of the vessel and restoration of the vessel's elasticity.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

Referring to the drawings, like numbers indicate like parts throughout the views.

DETAILED DESCRIPTION

Figure 1:
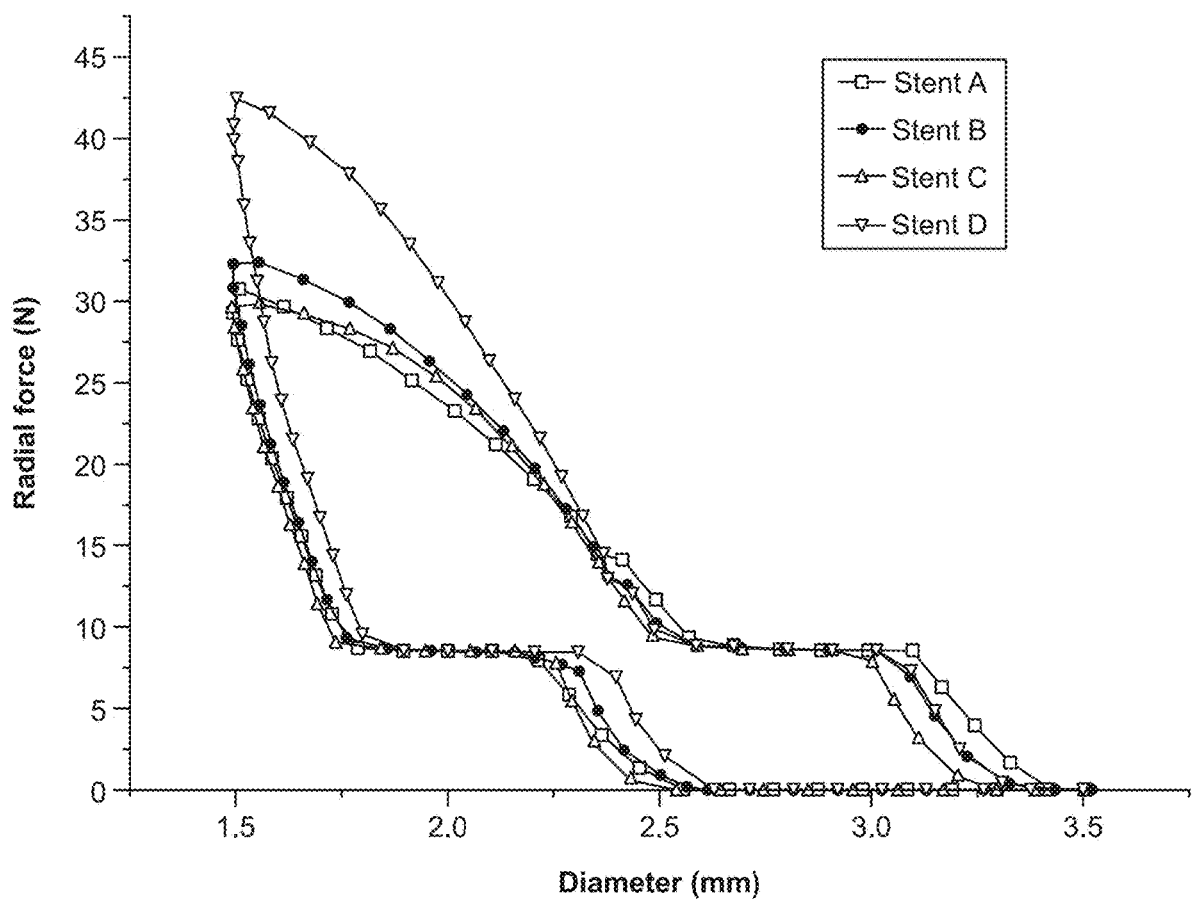
FIG. 1 shows the relationship between diameter and radial force in commercially available balloon-expandable coronary metal stents.
Figure 2:
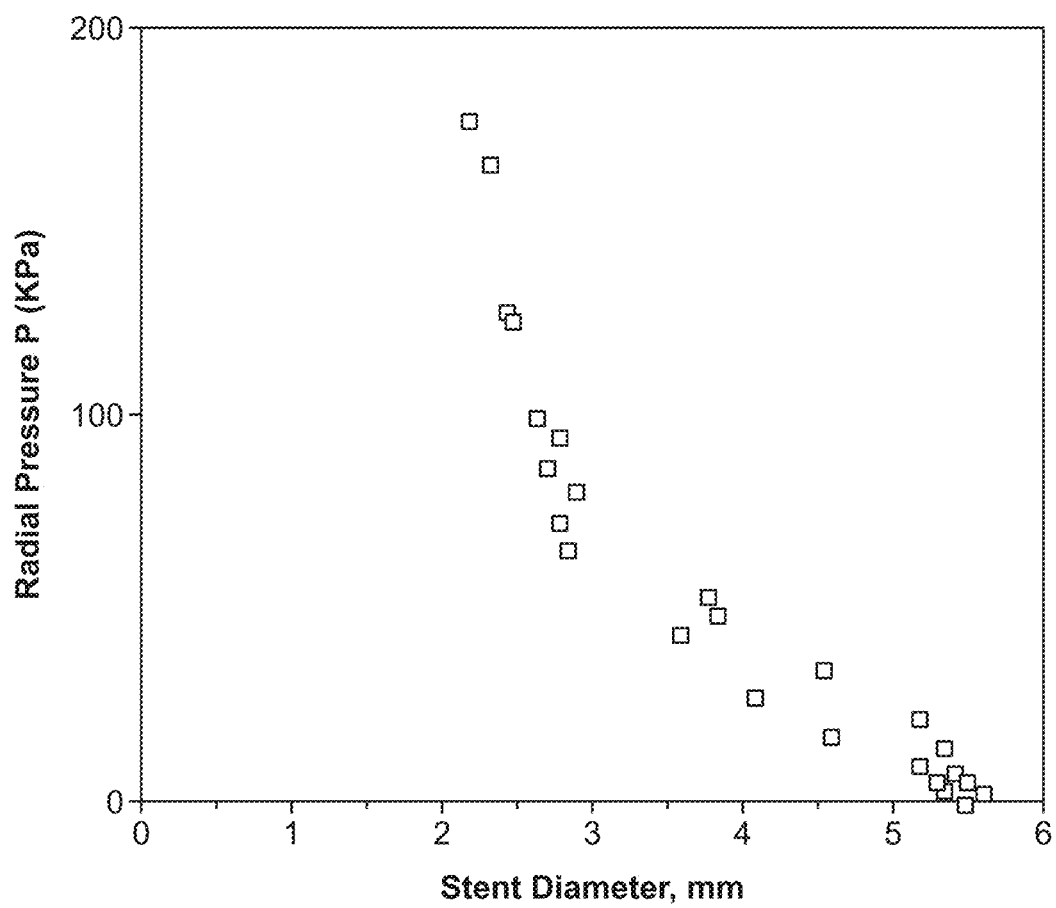
FIG. 2 shows the relationship between diameter and radial force in typical bioresorbable stents.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Various embodiments are described herein with reference to the figures. The figures are not drawn to scale and are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Figure 3:
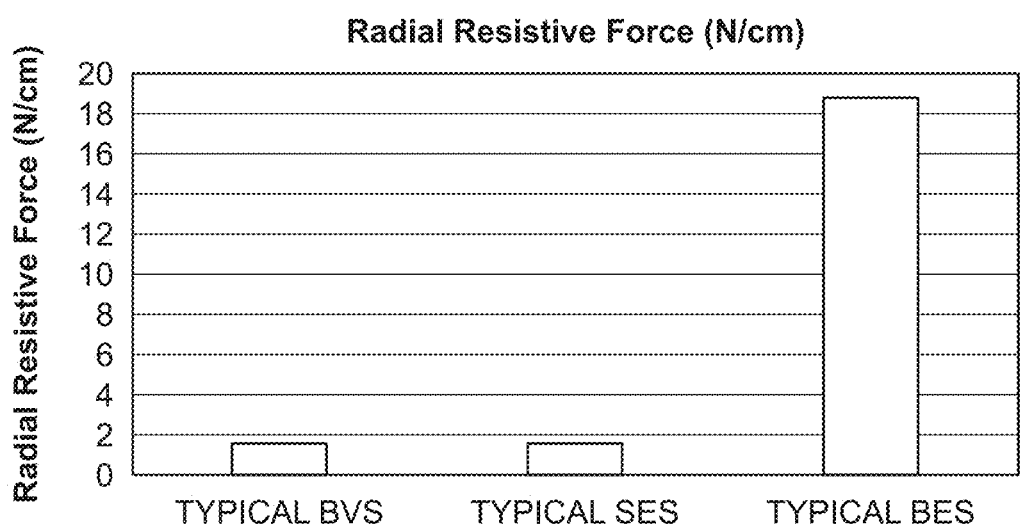
FIG. 3 shows the typical radial resistive forces of intravascular stents.

FIG. 3 shows the typical radial resistive forces of intravascular stents. A typical "bioresorbable vascular scaffold" (BVS) or absorbable stent has a radial resistive force of under 2 N/cm. Similarly, a typical self-expanding metal stent (SES) has a radial resistive force of under 2 N/cm. Typical balloon-expandable metal stents (BES) have a much higher radial resistive force, sometimes above 18 N/cm.

The embodiments herein describe the design of a new, intravascular absorbable device that maintains the flow channel (patency) of long blood vessels by providing temporary, rigid, radial support that is far greater than that provided by a typical absorbable or metal self-expanding stent (SES) and commensurate with that provided by a metal balloon-expandable stent (BES). Once implanted, the absorbable device imparts a high degree of radial force to prop open the diseased artery; the force is roughly equivalent to a large diameter, peripheral, balloon-expandable metal stent.

In contrast to most stent patterns which are designed to marry both radial force and longitudinal flexibility, the patterns described herein are specifically tailored to maximize radial force and rigidity and forego longitudinal and axial flexibility.

The devices described herein are multi-element, vascular stents (or "vascular scaffolds"). These stents are comprised of multiple, short, rigid, cylindrical stent segments, or elements, which are separate from one another but may be referred to together as a multi-element stent.

Generally, each element of the multi-element stents described herein will be sufficiently rigid to provide a desired level of strength to withstand the stresses of the vessel in which they are placed, such as a tortuous peripheral vessel. At the same time, a multi element stent will also be flexible, due to the fact that it is made up of multiple separate elements, thus allowing for placement within a curved, torturous blood vessel.

Additionally, the multi element stents described herein will usually be balloon-expandable rather than self-expanding, since balloon-expandable stents are typically stronger than self-expanding stents. Each balloon expandable element of the stent may have relatively high radial force (rigidity) due to the described structures and materials. A stent element is defined as being radially rigid if it has a radial strength significantly higher than self-expanding stents that is similar or greater in magnitude to that of traditional, metal balloon-expandable stents, such as those made of steel or cobalt-chromium.

When mounted serially on an inflatable balloon, they can be simultaneously implanted side-by-side in long blood vessels. During motion of the organism, the elements can move independently, maintaining their individual shape and strength while the intervening, non-stented elements of the vessel can twist, bend and rotate unencumbered. The result is a treated vessel with a rigidly maintained flow channel that still enjoys unrestricted flexibility during organismal movement.

The described embodiments exploit the principles that, (1) a rigid device that is deployed via balloon-expansion represents the optimal design of an intravascular stent given its transient effect on the arterial wall and relative ease of precise implantation, (2) a long, rigid device cannot be safely implanted in an artery that bends and twists with skeletal motion, (3) long arteries that bend and twist could be effectively treated with multiple, short BES that allow the intervening, non-stented arterial elements to move unencumbered, (4) the length, number and spacing of the stent elements could be determined by the known and predictable bending characteristics of the target arteries, and (5) arteries need only be scaffolded transiently; late dissolution of the stent will have little effect on the long-term effectiveness of treatment.

Figure 4A:
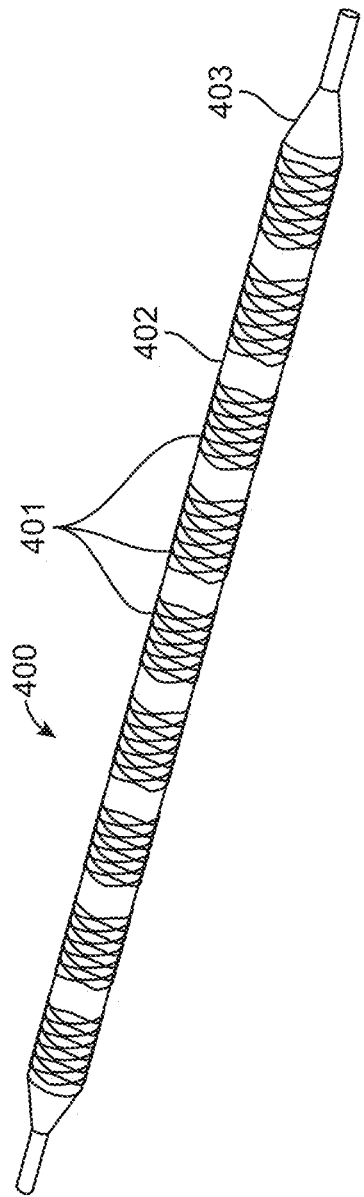
FIG. 4A illustrates one embodiment of a multi-element stent.

One embodiment of the fully assembled device in shown in FIG. 4A. A single balloon inflation and device deployment can treat a long segment of diseased artery while still preserving the critical ability of the artery to bend with skeletal motion such as sitting or walking. Multi-element stent 400 comprises multiple stent elements 401. Individual balloon-expandable stent elements 401 are crimped onto an inflatable balloon 403 to facilitate delivery.

Figure 4B:
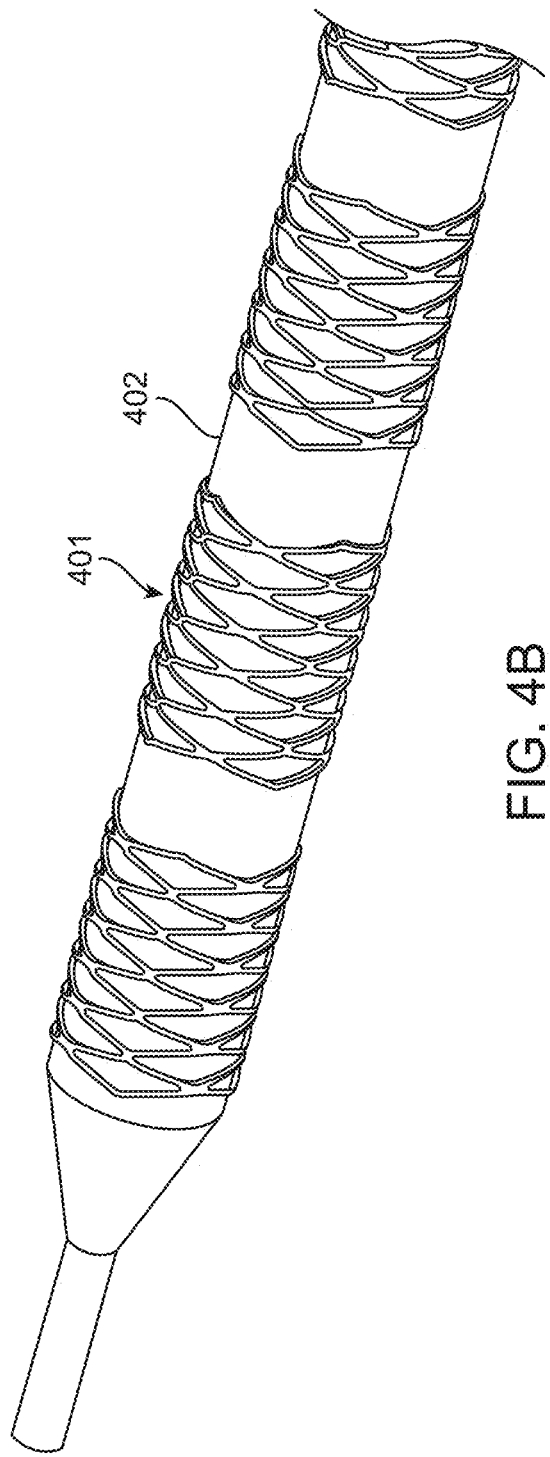
FIG. 4B is a magnified view of the stent elements in FIG. 4A.

FIG. 4B is a magnified view of the stent elements 401 in FIG. 4A. Individual elements 401 are positioned serially along a longitudinal length of the balloon 403 and spaced such that the stent elements 401 do not touch one another. Further, the spacing is such that after deployment, the stent elements 401 do not touch or overlap during skeletal movement. The number of elements 401, length of elements, and gap 402 between elements 401 may vary depending on the target vessel location. In an embodiment, each element 401 in the multi-element stent 400 has the same length. In multi-element stents having three or more elements 401, and thus two or more gaps 202, the gaps may be of the same length.

Figure 5A:
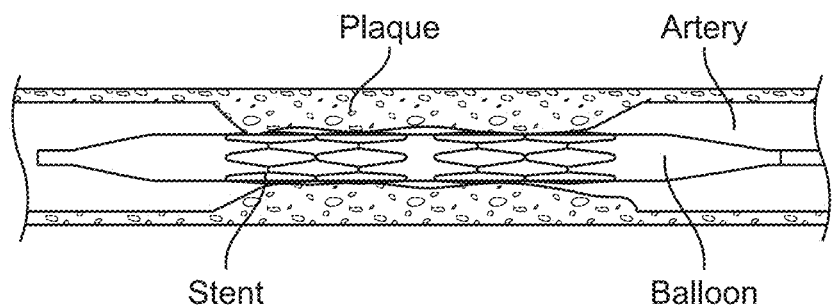
FIGS. 5A-5C depict deployment of a balloon-expandable multi-element stent.
Figure 5B:
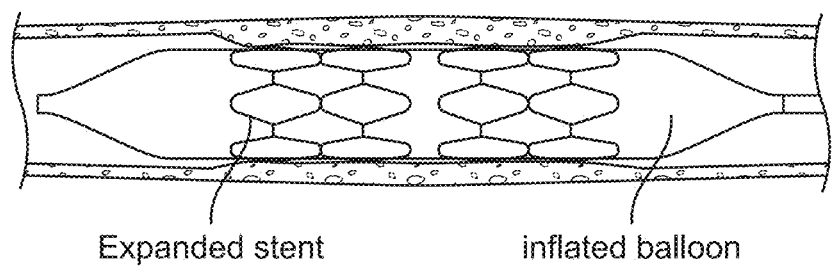
Figure 5C:
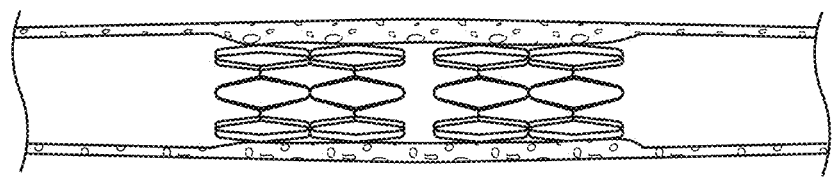

FIGS. 5A-5C depict deployment of a balloon-expandable multi-element stent. In FIG. 5A a multi-element stent mounted on a balloon is advanced to the lesion. In FIG. 5B the balloon and stent are expanded. In FIG. 5C the balloon is withdrawn leaving the multi-element stent still within the artery.

The stents described herein may be formed from various different materials. In an embodiment, stents may be formed a polymer. In various alternative embodiments, the stent or stent element may be made from any suitable bioresorbable material such that it will dissolve non-toxically in the human body, such as but not limited to poly(L-lactic acid) (PLLA), polyglycolic acid (PGA), poly(iodinated desaminotyrosyl-tyrosine ethyl ester) carbonate, or the like.

In alternative embodiments, any suitable polymer may be used to construct the stent. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable. For purpose of illustration and not limitation, the polymeric material may include, but is not limited to, poly(D-lactic acid) (PDLA), poly(D,L-lactic acid) (PDLLA), poly(iodinated desamino tyrosyl-tyrosine ethyl ester) carbonate, poly(lactic-co-glycolic acid) (PLGA), salicylate based polymer, semicrystalline polylactide, phosphorylcholine, polycaprolactone (PCL), poly-D,L-lactic acid, poly-L-lactic acid, poly(lactideco-glycolide), poly(hydroxybutyrate), poly(hydroxybutyrate-co-valerate), polydioxanone (PDS), polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material including acrylic polymers, and its derivatives, nylon, polyesters and expoxies. In some embodiments, the stent may include one or more coatings, with materials like poly(D,L-lactic acid) (PDLLA). These materials are merely examples, however, and should not be seen as limiting the scope of the invention.

Figure 6:
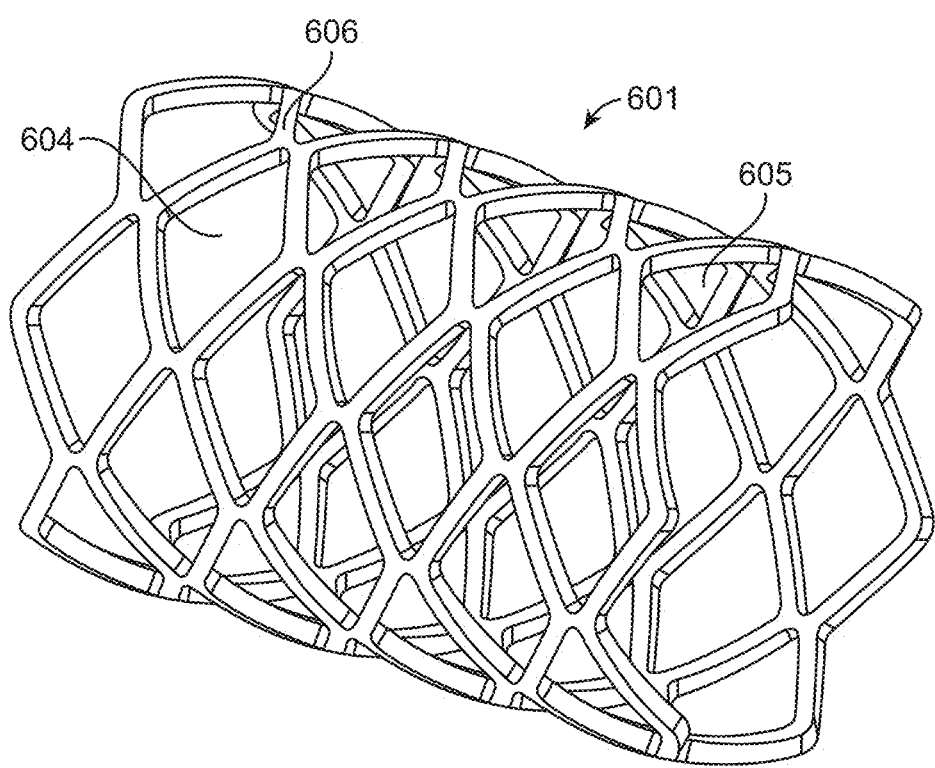
FIG. 6 shows an embodiment of a stent pattern designed for maximal radial force and stiffness when dilated to its nominal diameter.

One embodiment of a stent pattern designed for maximal radial force and stiffness when dilated to its nominal diameter is shown in shown in FIG. 6. The stent elements 601 have a diamond shaped closed-cell pattern with relatively thick strut widths and obliquely-angled links. Elements 601 comprise intermixed diamond shaped closed cells 604, 605. Elements 601 may comprise wide struts 606 of 225 microns or larger. Elements 601 may similarly comprise thick struts 606 of 225 microns or larger. In an embodiment, elements 601 comprise struts 606 with a width and/or thickness of approximately 250 microns. Diamond shaped cells 604 may be aligned in the longitudinal and/or the circumferential directions in a repeating pattern. Similarly, diamond shaped cells 605 may be aligned in the longitudinal and/or the circumferential directions in a repeating pattern. Additionally or alternatively, diamond shaped cells 604 and diamond shaped cells 605 may be helically aligned in an alternating pattern. In an embodiment, diamond shaped cells 604 and diamond shaped cells 605 are circumferentially offset. Additionally, diamond shaped cells 605 may be formed at a central location between four adjacent diamond shaped cells 604. The strength of element 601 is imparted through a design comprising tightly closed cells with relatively thick struts. When compressed radially (crimped), most of the struts are oriented horizontally or longitudinally. The compressed diameter may be approximately 2 mm (6 Fr). When expanded, however, the struts become oriented in the vertical or circumferential direction and, like the columns of a building, lend additional resistance to compression. The compressive load is spread throughout the repeating structure making it highly resistant to deformation. In an embodiment, the expanded nominal diameter is approximately 6 mm. Elements 601 may have a radial resistive force over 3 N/mm at the nominal diameter. In various embodiments, elements 601 may have a radial resistive force of between 3.5 N/mm and 4 N/mm at the nominal diameter. In an embodiment, elements 601 have a radial resistive force of approximately 3.8 N/mm at the nominal diameter.

Figure 7A:
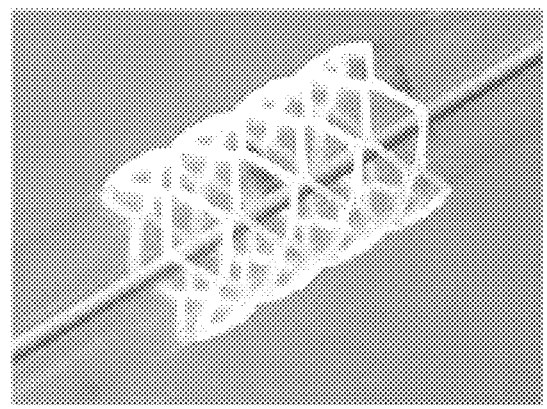
FIGS. 7A-7C shows a laser-cut bioresorbable stent comprised of a biologic polymer designed to generate its highest radial resistive force when expanded at or near its nominal diameter.
Figure 7B:
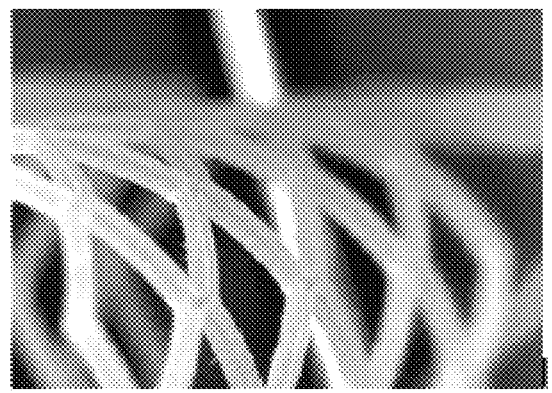
Figure 7C:
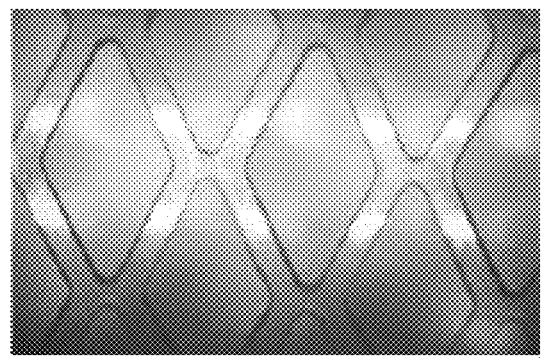

FIG. 7A shows a laser-cut bioresorbable stent comprised of a biologic polymer specifically designed to generate its highest radial resistive force when expanded at or near its nominal diameter. FIGS. 7B and 7C show magnified views of the stent in FIG. 7A.

Figure 8A:
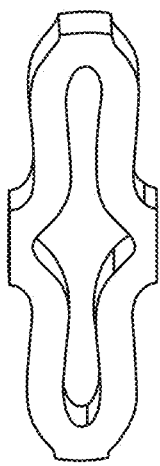
FIGS. 8A-8F show finite element analysis (FEA) of a bioresorbable polymer stent cell that vertically aligns with expansion.
Figure 8B:
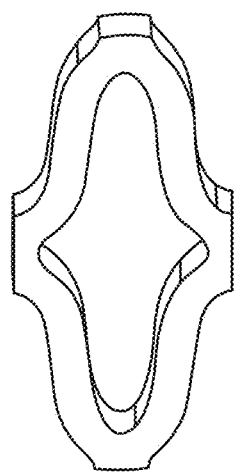
Figure 8C:
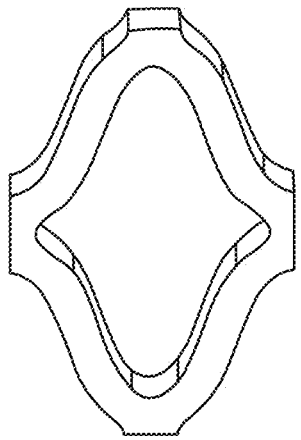
Figure 8D:
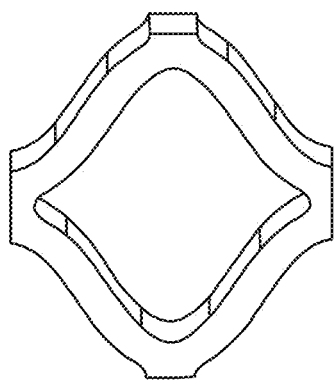
Figure 8E:
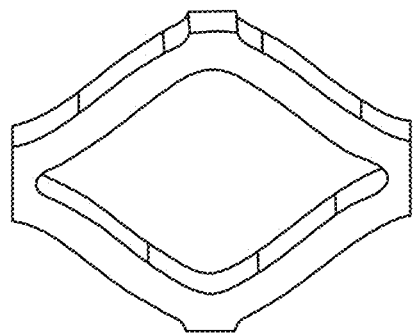
Figure 8F:
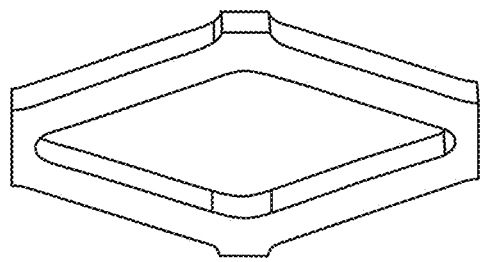

The change of angle that the struts undergo during expansion can be seen in FIGS. 8A-8F. FIGS. 8A-8F show 3D finite element analysis (FEA) of a bioresorbable polymer stent cell 804 that vertically aligns with expansion. Note that the primarily horizontally-aligned struts when fully crimped (FIG. 8A) slowly become vertically aligned upon expansion (FIG. 8F). This confers the property of maximal radial resistive force at the device's nominal diameter. Changing the length of struts or the number of cells circumferentially around the stent element can affect the change in angle.

Figure 9A:
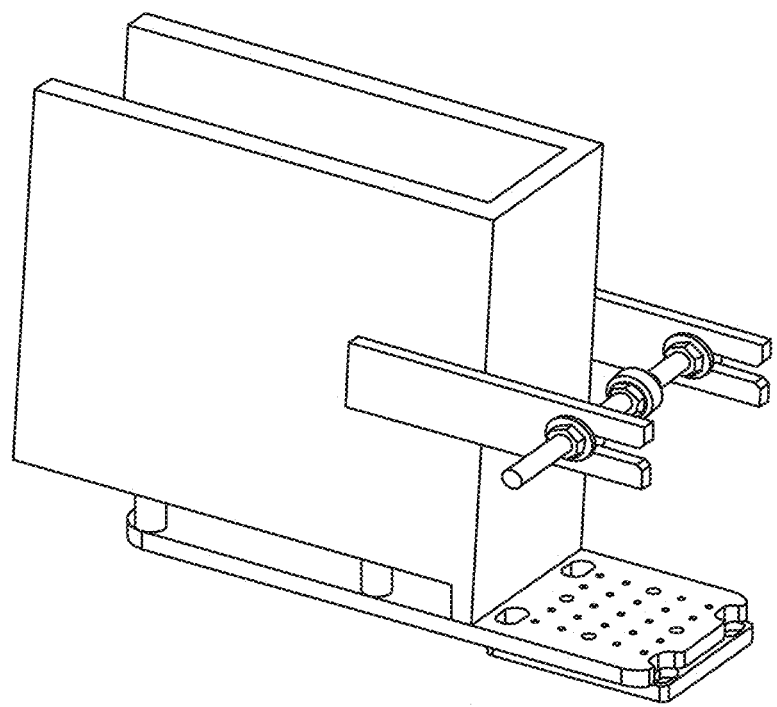
FIGS. 9A-9B show a circumferential radial force tester modified for compression of both resorbable scaffolds and metal stents.
Figure 9B:
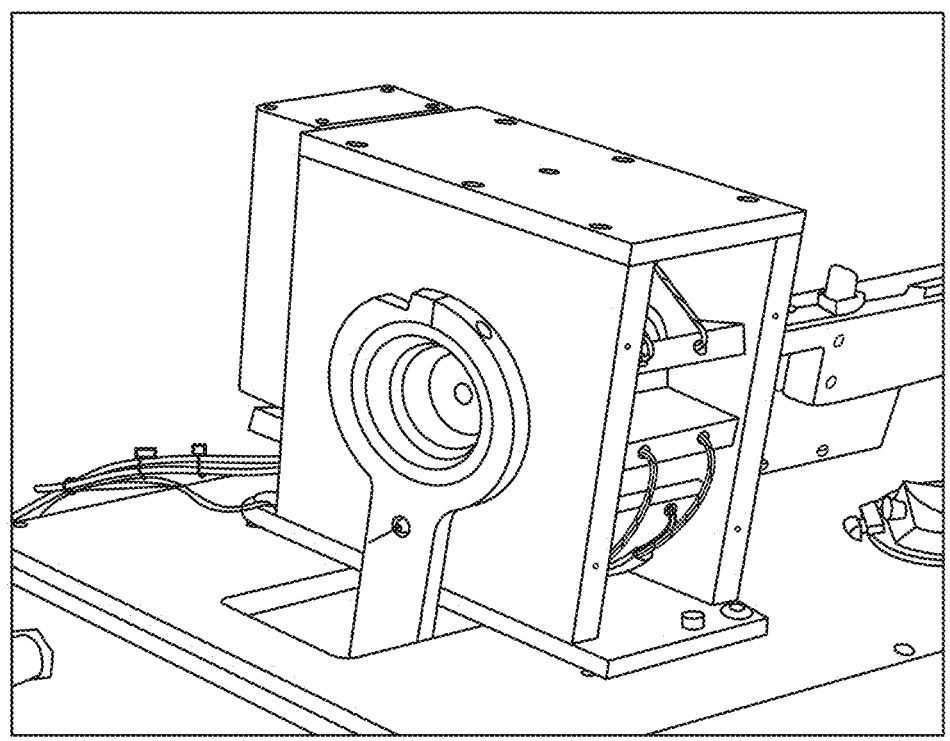
Figure 10:
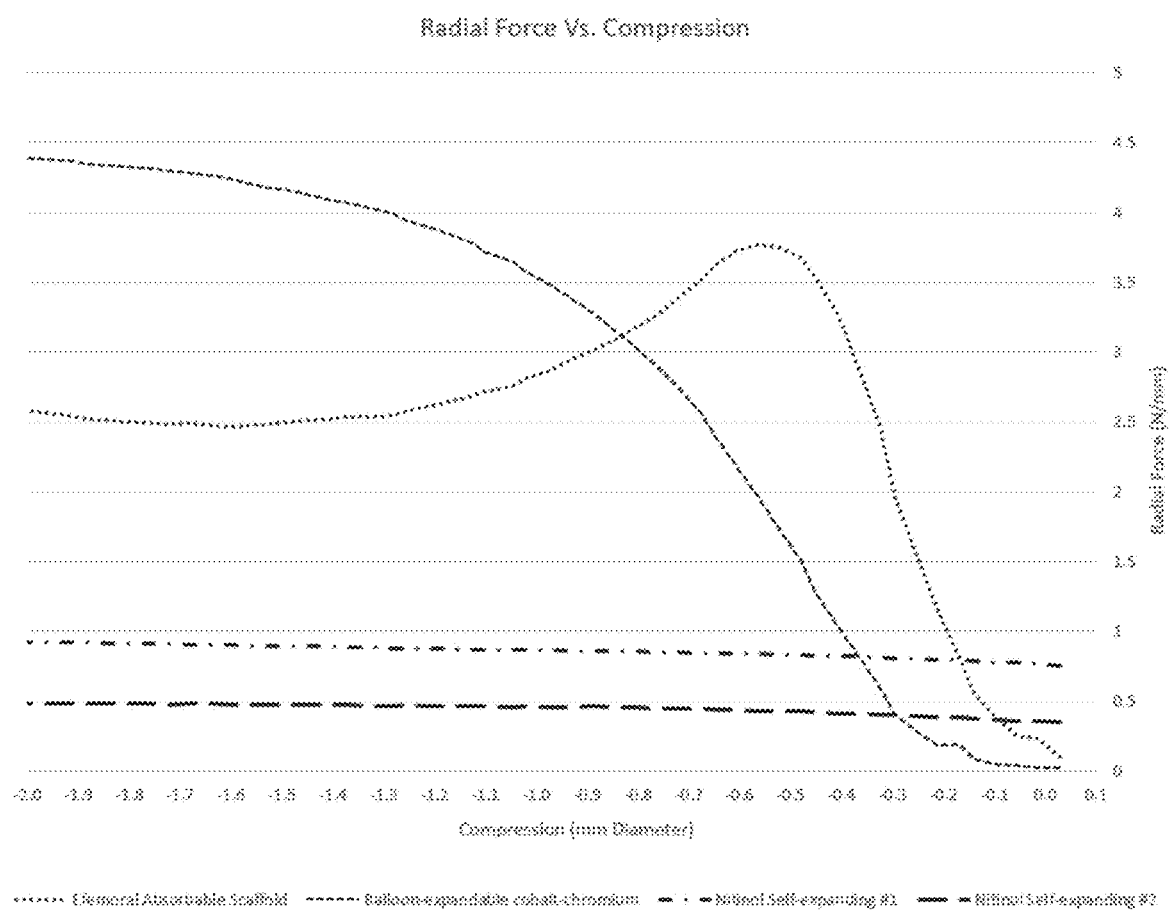
FIG. 10 shows radial force versus compression relationship for various intravascular devices.

An embodiment of the device was tested for radial strength (as a function of diameter) by modifying a specially-designed crimping device for this purpose shown in FIGS. 9A-9B. Absorbable scaffolds 6 mm in diameter (Efemoral Absorbable Scaffold), peripheral balloon-expandable cobalt-chromium stents 6 mm in diameter (Balloon-expandable cobalt-chromium) and nitinol self-expanding stents 8 mm (Nitinol Self-expanding #1, Nitinol Self-expanding #2) in diameter were tested. Each stent was expanded to its nominal diameter and placed in the circumferential radial force tester. The generated radial force was measured at 0.1 mm increments during continuous compression of the stent at a rate of 15 mm/s. The forces were recorded, divided by device length and plotted on the ordinate using diameter as the abscissa. The results are depicted in FIG. 10. The absorbable stents described herein generate peak radial resistive forces at or near their nominal diameters while balloon-expandable metal stents generate peak resistive forces only when compressed to smaller, non-clinically-relevant diameters. In one embodiment, the absorbable stent (Efemoral Absorbable Scaffold) generates peak radial resistive force which is quantitatively comparable to the force generated by the similarly-sized balloon-expandable metal device. However, the absorbable stent designed as described herein generates this resistive force at its nominal diameter; the diameter at which it will reside in the artery.

Figure 11:
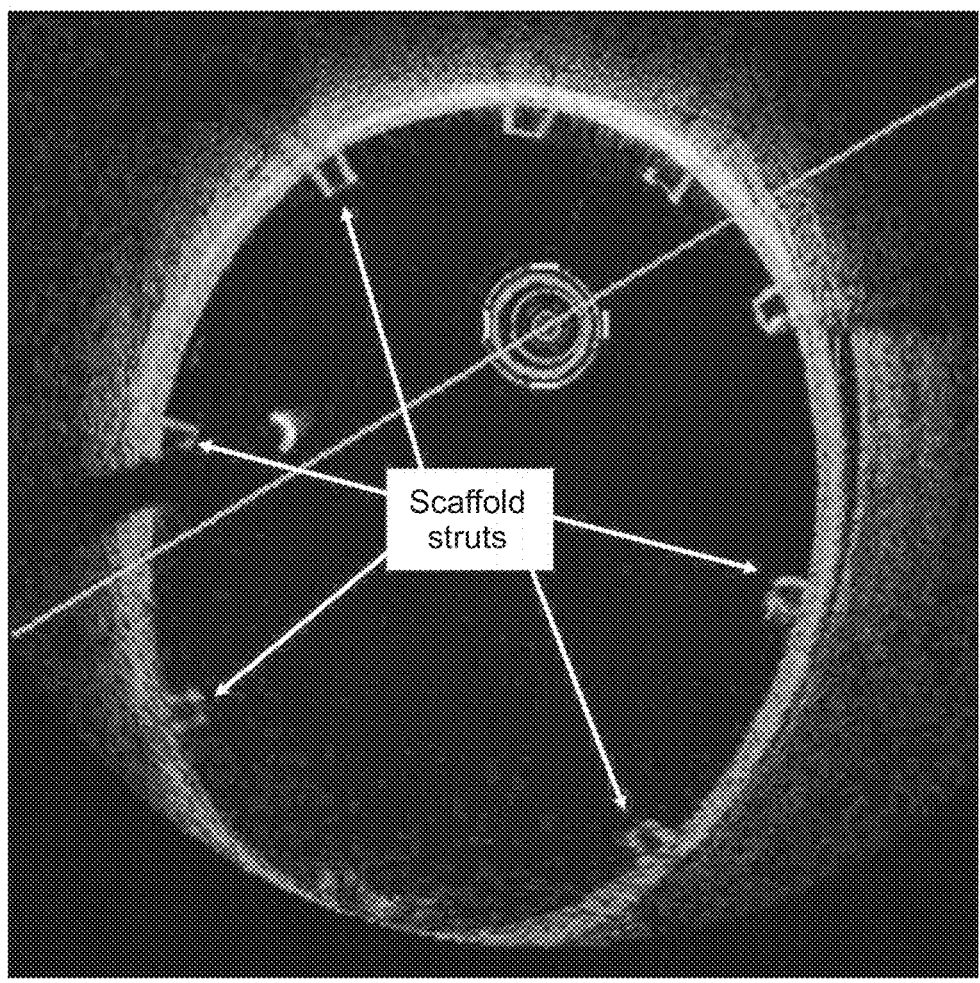
FIG. 11 shows an optical coherence tomographic (OCT) image of a deployed bioresorbable stent in the porcine iliofemoral artery.

The device and hypothesis were further tested by acute implantation into experimental animals. Domestic farm pigs were anesthetized with ketamine, azaperone and atropine administered intramuscularly. Via surgical exposure, a sheath was placed in the right common carotid artery and wire access of the left iliofemoral arterial system secured under fluoroscopic control. A two-segment device was deployed in the left iliofemoral artery. Following deployment, Optimal Coherence Tomographic (OCT) imaging was performed. The OCT catheter was advanced beyond the device, into the distal vessel, and pulled back to a point proximal to the device. An optical coherence tomographic (OCT) image of the deployed bioresorbable stent in the porcine iliofemoral artery is shown in FIG. 11. Note the thick struts of the fully-expanded stent abutting the arterial wall without malapposition.

The device described herein may include incorporation of a therapeutic drug intended to prevent or attenuate pathologic consequences of intraluminal intervention such as inflammation, cell dysfunction, cell activation, cell proliferation, neointimal formation, thickening, late atherosclerotic change and/or thrombosis. Any suitable therapeutic agent (or "drug") may be incorporated into, coated on, or otherwise attached to the stent, in various embodiments. Examples of such therapeutic agents include, but are not limited to, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, anti-neoplastics, agents that promote endothelial cell recovery, matrix metalloproteinase inhibitors, anti-metabolites, antiallergic substances, viral vectors, nucleic acids, monoclonal antibodies, inhibitors of tyrosine kinase, antisense compounds, oligonucleotides, cell permeation enhancers, hypoglycemic agents, hypolipidemic agents, proteins, nucleic acids, agents useful for erythropoiesis stimulation, angiogenesis agents, anti-ulcer/anti-reflux agents, and anti-nauseants/anti-emetics, PPAR alpha agonists such as fenofibrate, PPAR-gamma agonists selected such as rosiglitazaone and pioglitazone, sodium heparin, LMW heparins, heparoids, hirudin, argatroban, forskolin, vapriprost, prostacyclin and prostacylin analogues, dextran, D-phe-pro-arg-chloromethylketone (synthetic anti-thrombin), glycoprotein IIb/IIIa (platelet membrane receptor antagonist antibody), recombinant hirudin, thrombin inhibitors, indomethacin, phenyl salicylate, beta-estradiol, vinblastine, ABT-627 (astrasentan), testosterone, progesterone, paclitaxel, methotrexate, fotemusine, RPR-101511A, cyclosporine A, vincristine, carvediol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, and iotrolan, antisense compounds, inhibitors of smooth muscle cell proliferation, lipid-lowering agents, radiopaque agents, antineoplastics, HMG CoA reductase inhibitors such as lovastatin, atorvastatin, simvastatin, pravastatin, cerivastatin and fluvastatin, and combinations thereof.

Examples of antithrombotics, anticoagulants, antiplatelet agents, and thrombolytics include, but are not limited to, sodium heparin, unfractionated heparin, low molecular weight heparins, such as dalteparin, enoxaparin, nadroparin, reviparin, ardoparin and certaparin, heparinoids, hirudin, argatroban, forskolin, vapriprost, prostacyclin and prostacylin analogues, dextran, D-phe-pro-arg-chloromethylketone (synthetic antithrombin), dipyridamole, glycoprotein IIb/IIIa (platelet membrane receptor antagonist antibody), recombinant hirudin, and thrombin inhibitors such as bivalirudin, thrombin inhibitors, and thrombolytic agents, such as urokinase, recombinant urokinase, pro-urokinase, tissue plasminogen activator, ateplase and tenecteplase.

Examples of cytostatic or antiproliferative agents include, but are not limited to, rapamycin and its analogs, including everolimus, zotarolimus, tacrolimus, novolimus, and pimecrolimus, angiopeptin, angiotensin converting enzyme inhibitors, such as captopril, cilazapril or lisinopril, calcium channel blockers, such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, topoisomerase inhibitors, such as etoposide and topotecan, as well as antiestrogens such as tamoxifen.

Examples of anti-inflammatory agents include, but are not limited to, colchicine and glucocorticoids, such as betamethasone, cortisone, dexamethasone, budesonide, prednisolone, methylprednisolone and hydrocortisone. Non-steroidal anti-inflammatory agents include, but are not limited to, flurbiprofen, ibuprofen, ketoprofen, fenoprofen, naproxen, diclofenac, diflunisal, acetominophen, indomethacin, sulindac, etodolac, diclofenac, ketorolac, meclofenamic acid, piroxicam and phenylbutazone.

Examples of antineoplastic agents include, but are not limited to, alkylating agents including altretamine, bendamucine, carboplatin, carmustine, cisplatin, cyclophosphamide, fotemustine, ifosfamide, lomustine, nimustine, prednimustine, and treosulfin, antimitotics, including vincristine, vinblastine, paclitaxel, docetaxel, antimetabolites including methotrexate, mercaptopurine, pentostatin, trimetrexate, gemcitabine, azathioprine, and fluorouracil, antibiotics, such as doxorubicin hydrochloride and mitomycin, and agents that promote endothelial cell recovery such as estradiol.

Antiallergic agents include, but are not limited to, permirolast potassium nitroprusside, phosphodiesterase inhibitors, prostaglandin inhibitors, suramin, serotonin blockers, steroids, thioprotease inhibitors, triazolopyrimidine, and nitric oxide.

The beneficial agent may include a solvent. The solvent may be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetates, and combinations thereof.

Stents may be manufactured using an additive or a subtractive. In any of the described embodiments, stents or stent elements may be manufactured as a sheet and wrapped into cylindrical form. Alternatively, stents or stent elements may be manufactured in cylindrical form using an additive manufacturing process. In an embodiment, stents may be formed by extruding a material into a cylindrical tubing. In some embodiments, a longer stent element, may be formed during the manufacturing process and then cut into smaller stent elements/elements to provide a multi-element stent. In an embodiment, stent tubing may be laser cut with a pattern to form a stent element.

Figure 12:
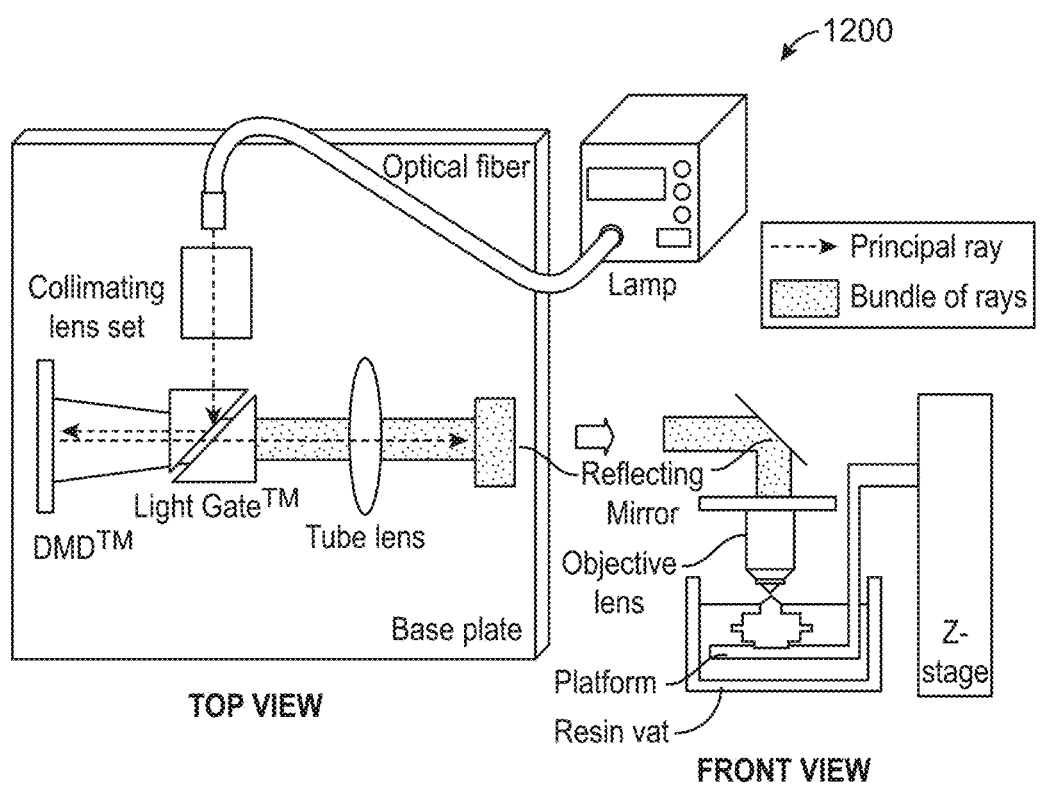
FIG. 12 is a schematic diagram of a micro-stereolithograph used to create a stent, according to one embodiment.

Referring now to FIG. 12, in one embodiment, stents may be manufactured using a micro-stereolithography system 1200 (or "3D printing system"). Several examples of currently available systems that might be used in various embodiments include, but are not limited to: MakiBox A6, Makible Limited, Hong Kong; CubeX, 3D Systems, Inc., Circle Rock Hill, SC; and 3D-Bioplotter, (EnvisionTEC GmbH, Gladbeck, Germany).

The micro-stereolithography system may include an illuminator, a dynamic pattern generator, an image-former and a Z-stage. The illuminator may include a light source, a filter, an electric shutter, a collimating lens and a reflecting mirror that projects a uniformly intense light on a digital mirror device (DMD), which generates a dynamic mask. FIG. 12 shows some of these components of one embodiment of the micro-stereolithography system 1200, including a DMD board, Z-stage, lamp, platform, resin vat and an objective lens. The details of 3D printing/micro-stereolithography systems and other additive manufacturing systems will not be described here, since they are well known in the art. However, according to various embodiments, any additive manufacturing system or process, whether currently known or hereafter developed, may potentially be used to fabricate stents within the scope of the present invention. In other words, the scope of the invention is not limited to any particular additive manufacturing system or process.

In one embodiment, the system 1200 may be configured to fabricate stents using dynamic mask projection micro-stereolithography. In one embodiment, the fabrication method may include first producing 3D microstructural scaffolds by slicing a 3D model with a computer program and solidifying and stacking images layer by layer in the system. In one embodiment, the reflecting mirror of the system is used to project a uniformly intense light on the DMD, which generates a dynamic mask. The dynamic pattern generator creates an image of the sliced section of the fabrication model by producing a black-and-white region similar to the mask. Finally, to stack the images, a resolution Z-stage moves up and down to refresh the resin surface for the next curing. The Z-stage build subsystem, in one embodiment, has a resolution of about 100 nm and includes a platform for attaching a substrate, a vat for containing the polymer liquid solution, and a hot plate for controlling the temperature of the solution. The Z-stage makes a new solution surface with the desired layer thickness by moving downward deeply, moving upward to the predetermined position, and then waiting for a certain time for the solution to be evenly distributed.

Although particular embodiments have been shown and described, they are not intended to limit the invention. Various changes and modifications may be made to any of the embodiments, without departing from the spirit and scope of the invention. The invention is intended to cover alternatives, modifications, and equivalents.

What is claimed is:

1. A device for placement within a blood vessel to maintain or enhance blood flow through the blood vessel, the device comprising:
   a balloon-expandable, bioresorbable, vascular stent element configured to be implanted in the blood vessel;
   wherein the stent element is formed from a bioresorbable polymer material;
   wherein the stent element is configured to have a compressed state with a first diameter while crimped on a delivery balloon before placement in the blood vessel and an expanded state with a second diameter greater than the first diameter after expansion and placement in the blood vessel;

wherein the stent elements comprise a closed cell pattern comprising diamond-shaped closed cells having four sides configured to provide a first radial resistive force in the compressed state and a second radial resistive force greater than the first radial resistive force in the expanded state; and wherein struts forming the four sides of the diamond-shaped closed cells are configured to have a substantially longitudinal alignment in the compressed state before placement in the blood vessel and a more circumferential alignment in the expanded state after expansion and placement in the blood vessel thereby the alignment of the struts forming the four sides of the diamond-shaped closed cells provide greater radial resistive force in the expanded state than the compressed state such that the second radial resistive force is above 3 N/mm and such that the stent elements have a peak radial resistive force at a diameter substantially equal to the second diameter.

2. The device of claim 1, further comprising a therapeutic drug, wherein the therapeutic drug prevents or attenuates inflammation, cell dysfunction, cell activation, cell proliferation, neointimal formation, thickening, late atherosclerotic change or thrombosis.

3. The device of claim 1, wherein the bioresorbable polymer material comprises poly (L-lactic acid) (PLLA), poly (D-lactic acid) (PDLA), poly (D,L-lactic acid) (PDLLA), semicrystalline polylactide, polyglycolic acid (PGA), poly (lactic-co-glycolic acid) (PLGA), poly (iodinated desamino tyrosyl-tyrosine ethyl ester) carbonate, polycaprolactone (PCL), salicylate based polymer, polydioxanone (PDS), poly (hydroxybutyrate), poly (hydroxybutyrate-co-valerate), polyorthoester, polyanhydride, poly (glycolic acid-co-trimethylene carbonate), poly (iodinated desaminotyrosyl-tyrosine ethyl ester) carbonate, polyphosphoester, polyphosphoester urethane, poly (amino acids), cyanoacrylates, poly (trimethylene carbonate), poly (iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, or combinations thereof.

4. The device of claim 1, wherein the radial rigidity of the device is attenuated as the bioresorbable polymer material is unlinked and metabolized such that the device becomes more flexible causing adaptation and remodeling of the vessel and restoration of the vessel's elasticity.

5. The device of claim 1, wherein the second diameter is 5.9-6.1 mm.

6. A device for placement within a blood vessel to maintain or enhance blood flow through the blood vessel, the device comprising:

a balloon-expandable, bioresorbable, vascular stent element configured to be implanted in the blood vessel;

wherein the stent element is formed from a bioresorbable polymer material;

wherein the stent element is configured to have a compressed state with a first diameter while crimped on a delivery balloon before placement in the blood vessel and an expanded state with a second diameter greater than the first diameter after expansion and placement in the blood vessel;

wherein the stent elements comprise a closed cell pattern comprising diamond-shaped closed cells having four sides configured to provide a first radial resistive force in the compressed state and a second radial resistive force greater than the first radial resistive force in the expanded state; and wherein struts forming the four sides of the diamond-shaped closed cells are configured to have a substantially longitudinal alignment in the compressed state before placement in the blood vessel and a more circumferential alignment in the expanded state after expansion and placement in the blood vessel thereby the alignment of the struts forming the four sides of the diamond-shaped closed cells provide greater radial resistive force in the expanded state than the compressed state such that the second radial resistive force is above 3 N/mm and such that the stent elements have a peak radial resistive force at a diameter within 0.1 mm of the second diameter.

* * * * *